United States Patent
Hayashi

(10) Patent No.: US 6,669,903 B2
(45) Date of Patent: Dec. 30, 2003

(54) BACTERICIDAL OR BACTERIOSTATIC METHOD

(75) Inventor: Michio Hayashi, 1-32-1012, Takasu-cho 2-chome, Nishinomiya-shi, Hyogo 663-8141 (JP)

(73) Assignees: Michio Hayashi, Hyogo (JP); Yokoyama Co., Ltd., Osaka (JP); Tsutae Kato, Nara (JP)

(*) Notice: Subject to any disclaimer, the term of this patent is extended or adjusted under 35 U.S.C. 154(b) by 404 days.

(21) Appl. No.: 09/872,674

(22) Filed: Jun. 1, 2001

(65) Prior Publication Data

US 2002/0098112 A1 Jul. 25, 2002

(30) Foreign Application Priority Data

Nov. 13, 2000 (JP) .................................. 2000-345802

(51) Int. Cl.⁷ .................................................. A61L 2/00
(52) U.S. Cl. .......................... 422/28; 422/1; 422/40; 424/404; 424/413; 514/57; 514/163; 514/506; 514/781
(58) Field of Search ................. 422/28, 1, 40; 514/57, 163, 506, 781; 424/404, 413

(56) References Cited

U.S. PATENT DOCUMENTS 4,331,728 A    5/1982    Theeuwes

FOREIGN PATENT DOCUMENTS

| FR | 1 590 713 | 4/1970 |
|---|---|---|
| JP | 3-227403 | 10/1991 |
| JP | 06-247815 | 9/1994 |
| JP | 07-82104 | 3/1995 |
| JP | 10-259531 | 9/1998 |
| JP | 2002-20524 | 1/2002 |
| JP | 2002-37706 | 2/2002 |
| JP | 2002-69437 | 3/2002 |
| RU | 2 146 264 | 3/2000 |
| WO | 99 20098 | 4/1999 |
| WO | 00 45804 | 8/2000 |

*Primary Examiner*—Krisanne Thornton
(74) *Attorney, Agent, or Firm*—Merchant & Gould P.C.

(57) ABSTRACT

Sterilization or bacteriostasis is carried out using cellulose acetate. The cellulose acetate exhibits an excellent antibacterial property with respect to fungi such as Trichophyton, etc. and bacteria such as, for example, enteropathogenic *Escherichia coli* O-157 or Methicillin tolerance *Staphylococcus aureus*. The cellulose acetate may be mixed with resin such as, for example, polyethylene or polypropylene, and this mixture may be used to produce fibers. Then, a textile product may be manufactured using the fibers thus produced. The cellulose acetate may be dissolved in a mixed solvent of ethyl acetate, ethanol, and methyl alcohol, so that a coating material is prepared. This coating material is applied to an object to be sterilized and then is dried to form a coating film made of cellulose acetate. This coating film exhibits the antibacterial property.

20 Claims, No Drawings

BACTERICIDAL OR BACTERIOSTATIC METHOD

BACKGROUND OF THE INVENTION

1. Field of the Invention

The present invention relates generally to a bactericidal or bacteriostatic method using cellulose acetate.

2. Related Background Art

Conventionally, inorganic antibacterial agents such as a silver compound or organic antibacterial agents containing an organic compound have been utilized as antibacterial agents used for sterilization or bacteriostasis. In addition, photocatalysts such as titanium oxide, etc. produce active oxygen by photoirradiation. This active oxygen provides an antibacterial action. Hence, titanium oxide or the like also may be used as antibacterial agents.

However, there has been a problem that conventional antibacterial agents have short lives. Accordingly, even when, for instance, resin products using such conventional antibacterial agents exhibit an antibacterial action at the beginning of use, various bacteria propagate or molds (fungi) grow after a certain period of time. Furthermore, conventional antibacterial agents include those that cannot provide effective sterilization or bacteriostatic actions against pathogenic bacteria including, for example, serious alimentary intoxication bacteria such as enteropathogenic *Escherichia coli* O-157 and methicillin resistant *Staphylococcus aureus* (MRSA). Even if the conventional antibacterial agents are effective for such bacteria, some of them may have harmful effects on human bodies. In order to provide a resin product or the like with an antibacterial property by using a conventional antibacterial agent, it has been necessary to add and knead the conventional antibacterial agent as an additive. When a sufficient antibacterial property is intended to be provided, it has been necessary to add and knead a large amount of antibacterial agent. This causes a disadvantage in cost and also affects the characteristics of the resin product. On the other hand, the photocatalysts do not allow an antibacterial action to be expressed without the help of light. Therefore, the use of such photocatalysts may be limited in some cases. Moreover, many of the conventional antibacterial agents are expensive and thus their use may be limited in view of their cost.

SUMMARY OF THE INVENTION

Therefore, with the foregoing in mind, it is an object of the present invention to provide a safe, simple, and inexpensive method enabling excellent long-term sterilization or bacteriostasis.

In order to achieve the above-mentioned object, the present invention is directed to a method in which cellulose acetate is used for sterilization or bacteriostasis.

The present inventor examined the antibacterial ability of natural organic substances to obtain an antibacterial substance that can solve all the aforementioned problems. As a result, he found out that cellulose acetate had excellent bactericidal and bacteriostatic ability. A particularly remarkable point is that the cellulose acetate exhibits an excellent bactericidal property even against the enteropathogenic *Escherichia coli* O-157, MRSA, and Trichophyton. The bactericidal or bacteriostatic property of the cellulose acetate remains as long as the cellulose acetate is present and accordingly, lasts for a long period. In addition, since the cellulose acetate is one type of resin, the cellulose acetate itself can be used for a resin product. Even when the cellulose acetate is mixed with other resins, there is a lower possibility that the cellulose acetate may affect the characteristics of the other resins, as compared to the case of conventional antibacterial agents. Moreover, the cellulose acetate is less expensive than the conventional antibacterial agents, is derived from a natural product, and has no safety problem, which has been proved by actual use over a long period.

It is not clear why the cellulose acetate exhibits the bactericidal or bacteriostatic property. However, the present inventor assumes that acetyl groups in the cellulose acetate cause the bactericidal property or the like to be expressed. In the following description, the term "antibacterial" includes the meanings of both "sterilization" and "bacteriostasis".

Preferably, the cellulose acetate used in the method of the present invention includes acetyl groups in a ratio of 1 to 3 per glucose residue, particularly preferably, in a ratio of 2.5 per glucose residue on average.

In the method of the present invention, preferably, the cellulose acetate is used together with boric acid. According to the knowledge that the present inventor has acquired, the cellulose acetate has an excellent antibacterial property against, for example, alimentary intoxication bacteria or pathogenic bacteria but is decomposed by *Bacillus subtilis*. This denotes that the cellulose acetate has a biodegradation property. This can be an advantage but also may be a disadvantage depending on the intended use. Hence, when the antibacterial action of the cellulose acetate is intended to be exhibited for a longer period of time, it is preferable that the cellulose acetate and boric acid (an antibacterial agent against the *Bacillus subtilis*) be used together as described above. The ratio of boric acid to be added to the cellulose acetate is, for example, 100 ppm to 1000 ppm, preferably 200 ppm to 600 ppm, and further preferably 200 ppm to 300 ppm.

DETAILED DESCRIPTION OF THE INVENTION

In the method of the present invention, the form of cellulose acetate to be used is not particularly limited. For example, the cellulose acetate may be used as an additive agent (an antibacterial agent) or may be processed into a plastic molded article, a coating material, a spray agent, or a textile product.

When used as an antibacterial agent, the cellulose acetate generally is present in a granular form. The grain size of such cellulose acetate is, for example, 0.001 to 5 mm, preferably, 0.001 to 2 mm, and further preferably 0.001 to 0.5 mm. The antibacterial agent may contain components other than the cellulose acetate, for example, a plasticizer such as phthalic acid. The granular antibacterial agent can be produced by, for example, a method including mixing a plasticizer (such as phthalic acid) with cellulose acetate (fine powder), kneading and extruding the mixture in a strand form with a twin screw extruder, and cutting it with a cutter. The mass ratio between the cellulose acetate and the plasticizer is as follows: for example, cellulose acetate:plasticizer=80:20.

Examples of items for which the cellulose acetate antibacterial agent can be used include resin products, coating materials, and textile products. When these products are produced, the antibacterial agent may be mixed with their main raw materials. Products thus obtained are provided with an excellent antibacterial property.

Next, in the method of the present invention, the cellulose acetate can be processed to form a plastic molded article. In this case, preferably, another resin is blended with the cellulose acetate depending on the intended use. Examples of another resin to be blended include thermoplastic resins such as polyethylene, polypropylene, polyvinyl chloride, polyvinylidene chloride, polystyrene, fluororesin, acrylic resin, methacrylic resin, polyvinyl acetate, polyamide, acetal resin, polycarbonate, polyphenylene oxide, polyester (polyethylene terephthalate, polybutylene terephthalate, aromatic polyester, polyallylate, etc.), polysulfone-based resin, and polyimide. Besides such thermoplastic resins, a thermosetting resin may be blended. Examples of such a thermosetting resin include phenolic resin, melamine resin, alkyd resin, unsaturated polyester resin, silicone resin, epoxy resin, urea resin, and urethane resin. The plastic molded article can be in a form of, for example, sheet, film, or rod, but is not particularly limited thereto. The ratio of the cellulose acetate in the plastic molded article is, for example, 1 to 100 mass %, preferably 10 to 100 mass %, and further preferably 30 to 100 mass %. For example, the methods of the examples described later can be used for processing the cellulose acetate into a plastic molded article.

Such a plastic molded article can be used variously depending on the intended use. For instance, in the case of a sheet- or film-like plastic molded article, such a plastic molded article may be allowed to adhere to the surface of another product as a protective material, so that the surface can be provided with an antibacterial property. A film made of cellulose acetate may be allowed to adhere to the surface of a product such as, for example, toilet articles, kitchen utensils, medical supplies, bath articles, or the like.

Next, in the method of the present invention, a coating material is prepared with cellulose acetate, and sterilization or bacteriostasis can be achieved using the coating material. Examples of a solvent used in the coating material include ethyl acetate, acetone, and chloroform. It also is preferable to blend an alcohol such as ethanol or methyl alcohol as a dissolution accelerator. This coating material can be manufactured through dissolution of cellulose acetate in a solvent. An example of the composition of this coating material is shown below. In the following composition, a total ratio of the respective components is 100 mass %.

Example of Coating Material Composition (unit: mass %)

| | General Range | Preferable Range | Optimum Range |
|---|---|---|---|
| Cellulose Acetate | 1 to 10 | 1 to 7 | 3.5 to 5 |
| Ethyl Acetate | 73 to 76 | 73 to 79 | 73 to 81 |
| Alcohol | 17 to 20 | 17 to 20 | 17 to 20 |

In the above-mentioned composition, preferably, the alcohol component is a mixed alcohol of ethanol and methyl alcohol. In this case, the weight ratio is as follows: for example, ethanol:methyl alcohol=90 to 100:10 to 0, preferably, 90 to 98:10 to 2, and more preferably 98 to 99:2 to 1. The use of ethanol allows a cellulose acetate coating film to be formed having excellent performance. This coating material may contain components other than the cellulose acetate and solvent. Such other components include, for example, pigment or dye.

When the coating material is applied to an object to be treated and then is dried, a coating film of cellulose acetate is formed and exhibits an antibacterial action. The antibacterial action lasts as long as this coating film is present. The method of applying the coating material is not particularly limited, and may be, for example, a brush application method, a method using a roll coater, or a dipping method. The object to be coated also is not limited, and may be, for example, toilet articles, kitchen utensils, medical supplies, bath articles, wallpaper, an inner side of a bathroom, joints between tiles in a bathroom or the like, passageways, closets, chests of drawers, or inner shelves of shoe cupboards or the like.

In the method of the present invention, a spray agent is prepared with cellulose acetate, and sterilization or bacteriostasis can be achieved using the spray agent. The spray agent can be produced by a method including preparing a coating material through dissolution of cellulose acetate in a solvent and filling a can with the coating material together with aerosol. The aforementioned solvents also can be used in this case. Examples of the aerosol include nitrogen gas, LPG, and DME. The blending ratio of the aerosol differs depending on the intended use, but is as follows: for example, coating material:spray gas=70 to 40%:30 to 60%. The method of filling a spray can with the spray agent is a conventional method and the pressure used therein is, for example, 0.3 to 0.5 MPa. In the method of using the spray agent, it is only necessary to blow it on the object to be treated. When the solvent is dried, a cellulose acetate coating film is formed and exhibits the antibacterial action. Examples of the object to be treated are the same as in the case of using the coating material.

Next, in the method of the present invention, cellulose acetate is processed to form fibers, and sterilization or bacteriostasis can be achieved using the fibers. In this case, such fibers may be formed of cellulose acetate alone like acetate fibers, or may be formed of a mixture of cellulose acetate and another resin. When a textile product is manufactured, fibers made of cellulose acetate may be mixed with other fibers and the mixed fibers may be used for the manufacture. The size of the fibers is not particularly limited.

When being formed of cellulose acetate alone, fibers can be manufactured using cellulose, for example, in the same manner as in the case of acetate fibers or triacetate fibers. Initially, the cellulose is esterified with acetic anhydride. Then, the cellulose thus esterified is hydrolyzed partially to have an esterification degree of 55 to 60%, which then is dissolved in acetone. This is spun by a dry spinning method and thus acetate fibers can be obtained. Furthermore, cellulose is esterified with acetic anhydride and thereby triacetate is obtained. This is dissolved in a mixed solvent of methylene chloride and methyl alcohol, which then is spun by the dry spinning method. Thus, triacetate fibers can be obtained.

Fibers made of cellulose acetate can be used for various applications. Application examples follow:

general clothing lining of European clothes and Japanese clothes (kimonos)

bedding such as bedsheets, pillow cases, pyjamas underwear, insoles of shoes, etc.

diapers, sanitary goods towels, bath towels, handkerchieves, dish towels, small towels to be served to guests in a wet state at table, etc.

inner bottom covers for chests of drawer, closets or the like, suit covers curtains, carpets, center rugs, covers for electric carpets, covers for cushions, covers for "kotatsu (a Japanese foot warmer with a quilt over it)" coverlets, tablecloths, luncheon mats filter sheets of purifiers for city water respirators, dressings, cloth portions of first-aid bandages or eye bandages handles of bags or suitcases, covers for leather goods containers for keeping small articles such as cosmetics (accessory cases)

dust-proof covers (for example, covers for electric fans, toasters, rice cookers, etc.)

The whole or part of each textile product mentioned above may be formed of fibers made of cellulose acetate. For instance, since the cellulose acetate gives an excellent antibacterial action against Trichophyton, the whole sock may be formed of cellulose acetate fibers or only a portion thereof coming into contact with toes may be formed of the cellulose acetate fibers and the other portion may be formed of, for example, nylon fibers with high strength.

EXAMPLES

The following description is directed to examples of the present invention.

Example 1

Cellulose acetate (fine powder) and a plasticizer (for example, phthalic acid) were blended. This blend was kneaded and extruded in a strand form with a twin screw extruder and then was cut with a cutter. Thus, a pellet was obtained. The mass ratio between the cellulose acetate and the plasticizer was as follows: cellulose acetate:plasticizer= 80:20. This pellet was kneaded and then was extruded in a sheet form with a twin-screw T-die extruder (at a temperature of 185 to 225° C.). Thus, a sheet with a thickness of 0.6 mm was obtained. The antibacterial property of this sheet was checked. The result is shown in Table 1.

Antibacterial Property Testing Method

*Escherichia coli* (O-157:H7), Salmonella, and *Vibrio parahaemolyticus* were used for the test. A solution for preparing a bacterium liquid was prepared as follows: with respect to the *Escherichia coli* and Salmonella, an NB culture medium was diluted with purified water to $\frac{1}{5000}$, and with respect to the *Vibrio parahaemolyticus*, an NB culture medium with 3% NaCl added thereto was diluted with purified water to $\frac{1}{200}$. The testing method was a film adhesion method. As a control, a polyethylene film was used. The film adhesion method is a testing method instituted by Antibacterial Product Engineering Council. In the film adhesion method, the test is carried out by dropping a bacterium liquid on a culture medium and then allowing a film, a sheet, or the like to adhere to the culture medium. The culture medium to be used also is prescribed in this testing method. The final culture medium is a standard agar medium.

TABLE 1

| Tested Bacteria | Measurement | Sample | Viable Count per Sample |
|---|---|---|---|
| *Escherichia Coli* (O-157:H7) | Directly After Inoculation 35° C. | Control Specimen | $1.6 \times 10^5$ <10 |
|  | After 24 Hours | Control | $9.5 \times 10^6$ |
| Salmonella | Directly After Inoculation 35° C. | Control Specimen | $4.7 \times 10^5$ <10 |
|  | After 24 Hours | Control | $6.1 \times 10^5$ |
| *Vibrio Parahaemolyticus* | Directly After Inoculation 35° C. | Control Specimen | $1.9 \times 10^5$ <10 |
|  | After 24 Hours | Control | $1.5 \times 10^5$ |

Example 2

A coating piece and a film were produced by the following production methods and antibacterial properties thereof were checked. The results are shown in Table 2.

Coating Piece Production Method

A coating material with the following composition was prepared and was applied to the surface of a reed pulp container. Afterward, the solvent and alcohol were dried to be removed. Accordingly, the coating film on the coating piece is formed of cellulose acetate alone.

| Composition | |
|---|---|
| Cellulose Acetate | 1 to 10% |
| Ethyl Acetate | 73 to 76% |
| Mixed Alcohol | 17 to 20% (Ethanol:Methyl Alcohol = 98:2) |

Film Production Method

Cellulose acetate (fine powder) and a plasticizer (for example, phthalic acid) were blended. This blend was kneaded and extruded in a strand form with a twin screw extruder and then was cut with a cutter. Thus, a pellet was obtained. The mass ratio between the cellulose acetate and the plasticizer was as follows: cellulose acetate:plasticizer= 80:20. This pellet was kneaded and then was blown up in a film form with a twin-screw inflation extruder (at a temperature of 185 to 225° C.). Thus, a film with a thickness of 30 to 40 μmm was obtained.

Antibacterial Property Testing Method

The antibacterial property was checked by the aforementioned film adhesion method using the following bacteria and a culture medium. A commercial polyethylene bag was used as a control. The surface of a coating piece was used for the test.

Testing Bacteria

*Staphylococcus aureus* (IFO 12732)

*Escherichia coli* (IFO 3972)

Methicillin resistant *Staphylococcus aureus* (MRSA) (IID 1677)

*Pseudomonas aeruginosa* (IFO 3080)

*Escherichia coli* O-157:H7 (ATCC 43888)

TABLE 2

| Sample | Viable Count | Variation Value |
|---|---|---|
| *Staphylococcus aureus* | | |
| Control Directly After Inoculation | $4.9 \times 10^5$ | — |
| Control | $1.6 \times 10^6$ | — |
| Blank | $1.5 \times 10^6$ | — |
| Coating Piece | $4.6 \times 10^4$ | 1.5 |
| *Escherichia coli* | | |
| Control Directly After Inoculation | $2.9 \times 10^5$ | — |
| Control | $2.0 \times 10^7$ | — |
| Blank | $2.1 \times 10^7$ | — |
| Coating Piece | $8.2 \times 10^4$ | 2.4 |
| MRSA | | |
| Control Directly After Inoculation | $3.4 \times 10^5$ | — |
| Control | $1.2 \times 10^7$ | — |
| Blank | $1.3 \times 10^7$ | — |
| Film | $5.7 \times 10^3$ | 3.3 |
| *Pseudomonas aeruginosa* | | |
| Control Directly After Inoculation | $2.8 \times 10^5$ | — |
| Control | $2.6 \times 10^6$ | — |

TABLE 2-continued

| Sample | Viable Count | Variation Value |
|---|---|---|
| Blank | $3.8 \times 10^6$ | — |
| Film | $1.6 \times 10^4$ | 2.3 |
| *Escherichia coli* | | |
| Control Directly After Inoculation | $1.3 \times 10^5$ | — |
| Control | $4.5 \times 10^6$ | — |
| Blank | $3.8 \times 10^6$ | — |
| Film | $8.3 \times 10^2$ | 3.6 |

Example 3

A foamed body was produced by the following method and its fungus resistance and antibacterial property were checked by the following methods. The results are shown in Tables 3 and 4 below. This foamed material had a composition of cellulose acetate:polypropylene=50:50.

Production Method

A material (plasticizer) containing 20 mass parts polyethylene glycol with a molecular weight of 400 or less mixed with 10 mass parts water was kneaded with 100 mass parts cellulose acetate (fine powder). In order to obtain a sufficient plastic efficient, after being left standing for about 30 minutes, the kneaded material was mixed with polypropylene. This mixture was introduced into a twin-screw foaming extruder and was foam-extruded in a sheet form (at a temperature of 185 to 225° C.). Thus, a sheet-like foamed body was obtained.

Fungus Resistance Testing Method

Fungus resistance was checked according to the method prescribed in Japanese Industrial Standard (JIS) Z 2911.5. The following testing bacteria and evaluation criteria were used in this method.

Bacteria used for Fungus Resistance Test

*Aspergillus niger* (IFO 6341)
*Penicillium citrinum* (IFO 6352)
*Rhizopus stolonifer* (IFO 31005)
*Cladosporium cladosporioides* (IFO 6348)
*Chaetomium globosum* (IFO 6347)

Fungus Resistance Evaluation Criteria

1: The portion of a specimen where hypha had grown was observed in an area exceeding one third of the whole area.
2: The portion of a specimen where hypha had grown was observed in an area of one third of the whole area or less.
3: No growth of hypha was observed on a specimen.

Antibacterial Property Test

The antibacterial property was evaluated by a dropping test. This dropping test is instituted by Antibacterial Product Engineering Council. The dropping test was carried out by dropping a bacterium liquid directly on a sample and then checking the residual bacteria. The culture medium to be used also is prescribed in this testing method. The final culture medium is a standard agar medium. A commercial polyethylene bag was used for the test as a blank sample.

The testing bacteria follow.
Bacteria used for Antibacterial Property Test
*Staphylococcus aureus* (IFO 12732)
Methicillin resistant *Staphylococcus aureus* (MRSA) (IID 1677)

TABLE 3

| | Fungus Resistance | | |
|---|---|---|---|
| | After 2 Weeks | After 4 Weeks | Remarks |
| Evaluation | 3 | 3 | No growth of fungus |

TABLE 4

| Antibacterial Property | | |
|---|---|---|
| Sample | Viable Count | Variation Value |
| *Staphylococcus Aureus* | | |
| Control Directly After Inoculation | $4.9 \times 10^5$ | — |
| Control | $1.9 \times 10^6$ | — |
| Blank | $1.2 \times 10^6$ | — |
| Foamed Body | 10 or less | At least 5.0 |
| MRSA | | |
| Control Directly After Inoculation | $4.1 \times 10^5$ | — |
| Control | $6.9 \times 10^5$ | — |
| Blank | $4.4 \times 10^3$ | — |
| Foamed Body | $4.7 \times 10^2$ | 0.9 |

Example 4

A test piece (a plate) was produced by the following production method and the fungus resistance thereof was checked by the same method as described above. The result is shown in Table 5 below.

Production Method

Cellulose acetate (fine powder) and a plasticizer (for example, phthalic acid) were blended. The blend was kneaded and extruded in a strand form with a twin screw extruder and then was cut with a cutter. Thus, a pellet was obtained. The mass ratio between the cellulose acetate and the plasticizer was as follows: cellulose acetate:plasticizer= 80:20. Then, 10 mass parts of this pellet was blended with 90 mass parts polypropylene. This blend was injection-molded in a plate form with an injection molding machine. Thus, a plate with a thickness of 2 mm was obtained.

TABLE 5

| | Fungus Resistance | | |
|---|---|---|---|
| | After 2 Weeks | After 4 Weeks | Remarks |
| Evaluation | 3 | 3 | No growth of fungus |

Example 5

With respect to commercial acetate fiber (manufactured by Teijin Limited under a product name of Teijin Acetate), its Trichophyton resistance and antibacterial property were checked by the following methods. As a result, a growth inhibition zone had a width of 1.8 mm in the Trichophyton resistance test. The test result of the antibacterial property is shown in Table 6.

Trichophyton Resistance Testing Method

This test was carried out by a halo test according to JIS L 1902. More specifically, when a sample was brought into close contact with a culture medium, an antibacterial agent flowed out from the sample and a transparent growth inhibition zone was formed. Then, this inhibition zone (halo) was measured. The acetate fiber was regarded as having the Trichophyton resistance as long as the inhibition zone was formed even only slightly. The culture medium to be used also is prescribed in this testing method. The final culture medium was a PDA agar medium. The test bacterium was *Trichophyton mentagrophytes* (IFO 6202).

Antibacterial Property Testing Method

The antibacterial property was checked by the unified testing method according to JIS L 1902. More specifically, the testing method was carried out by dropping a bacterium liquid on the culture medium and bringing a fiber sample into close contact therewith. The culture medium to be used also is prescribed in this testing method. The final culture medium was a nutrient agar medium. The following testing bacteria were used and a standard nylon white cloth was used as a blank.

*Escherichia coli* (IFO 3301)

*Staphylococcus aureus* (ATCC 6538P)

Methicillin resistant *Staphylococcus aureus* (MRSA) (IID 1677)

TABLE 6

Antibacterial Property

| Sample | Viable Count | Bacteriostatic Activity Value | Bactericidal Activity Value |
|---|---|---|---|
| *Staphylococcus Aureus* | | | |
| Acetate Fiber | 20 or less | at least 5.8 | at least 3.0 |
| Blank Directly After Inoculation | $1.8 \times 10^4$ | | |
| Blank After 18 Hours | $1.3 \times 10^7$ | | |
| *Escherichia Coli* | | | |
| Acetate Fiber | 20 or less | at least 6.0 | at least 3.0 |
| Blank Directly After Inoculation | $1.8 \times 10^4$ | | |
| Blank After 18 Hours | $2.0 \times 10^7$ | | |
| MRSA | | | |
| Acetate Fiber | 20 or less | at least 5.7 | at least 3.1 |
| Blank Directly After Inoculation | $2.6 \times 10^4$ | | |
| Blank After 18 Hours | $9.2 \times 10^6$ | | |

From the results of the examples described above, it can be said that the cellulose acetate exhibits an excellent antibacterial property with respect to fungi including Trichophyton and bacteria including pathogenic bacteria.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A bactericidal or bacteriostatic method, comprising bringing cellulose acetate into contact with an object to be subjected to sterilization or bacteriostasis in an amount sufficient to provide a sterilizing bacteriostatic property.

2. The bactericidal or bacteriostatic method according to claim 1, wherein the cellulose acetate has a form of granule, fiber, sheet, or film.

3. The bactericidal or bacteriostatic method according to claim 1, wherein the cellulose acetate has 2.5 acetyl groups per glucose residue on average.

4. A bactericidal or bacteriostatic method, comprising bringing a resin molded article formed of cellulose acetate and resin into contact with an object to be subjected to sterilization or bacteriostasis, the cellulose acetate being contained in an amount sufficient to provide a sterilizing bacteriostatic property.

5. The bactericidal or bacteriostatic method according to claim 4, wherein the resin is at least one of polyethylene and polypropylene.

6. The bactericidal or bacteriostatic method according to claim 4, wherein the resin molded article further comprises a plasticizer.

7. The bactericidal or bacteriostatic method according to claim 4, wherein the resin molded article further comprises boric acid.

8. The bactericidal or bacteriostatic method according to claim 4, wherein the resin molded article has a form of granule, fiber, sheet, or film.

9. The bactericidal or bacteriostatic method according to claim 4, wherein the cellulose acetate has 2.5 acetyl groups per glucose residue on average.

10. A bactericidal or bacteriostatic method, comprising applying a solution containing cellulose acetate dissolved in a solvent to an object to be subjected to sterilization or bacteriostasis, in an amount sufficient to provide a sterilizing bacteriostatic property.

11. The bactericidal or bacteriostatic method according to claim 10, wherein the solution applied is dried to form a coating film of the cellulose acetate on a surface of the object, and sterilization or bacteriostasis is achieved with the coating film.

12. The bactericidal or bacteriostatic method according to claim 10, wherein the solvent is at least one selected from a group consisting of ethyl acetate, acetone, and chloroform.

13. The bactericidal or bacteriostatic method according to claim 10, wherein the solution further comprises a liquid mixture of methyl alcohol and ethanol.

14. The bactericidal or bacteriostatic method according to claim 11, wherein the solution further comprises boric acid.

15. The bactericidal or bacteriostatic method according to claim 10, wherein the cellulose acetate has 2.5 acetyl groups per glucose residue on average.

16. A bactericidal or bacteriostatic method, comprising:

applying a mixture of cellulose acetate, a solvent, and an aerosol to an object to be subjected to sterilization or bacteriostasis by spraying in an amount sufficient to provide a sterilizing bacteriostatic property.

17. The bactericidal or bacteriostatic method according to claim 16, wherein the solution applied is dried to form a coating film of the cellulose acetate on a surface of the object, and sterilization or bacteriostasis is achieved with the coating film.

18. The bactericidal or bacteriostatic method according to claim 16, wherein the aerosol is liquefied petroleum gas (LPG).

19. The bactericidal or bacteriostatic method according to claim 17, wherein boric acid further is included in the mixture.

20. The bactericidal or bacteriostatic method according to claim 16, wherein the cellulose acetate has 2.5 acetyl groups per glucose residue on average.

\* \* \* \* \*